Figure 1:
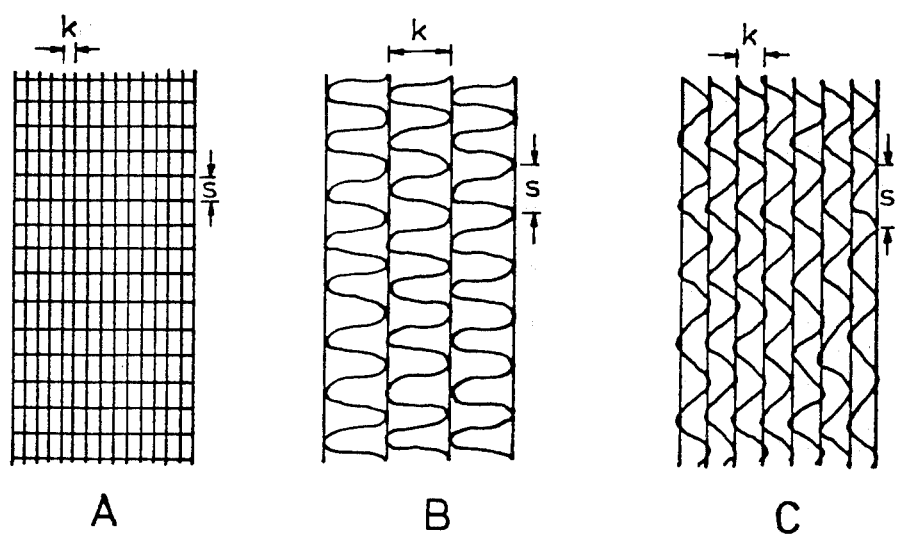

United States Patent [19]

Wegner et al.

[11] Patent Number: 4,572,171

[45] Date of Patent: Feb. 25, 1986

[54] POLYURETHANE FIXED DRESSINGS WHICH HARDEN IN THE PRESENCE OF MOISTURE

[75] Inventors: Christian Wegner, Cologne; Gottfried Schneider, Leverkusen; Wolfram Mayer, Bergisch-Gladbach, all of Fed. Rep. of Germany

[73] Assignee: Bayer Aktiengesellschaft, Leverkusen, Fed. Rep. of Germany

[21] Appl. No.: 476,094

[22] Filed: Mar. 17, 1983

[30] Foreign Application Priority Data

Mar. 30, 1982 [DE] Fed. Rep. of Germany ....... 3211634

[51] Int. Cl.$^4$ ................................................ A61F 5/04
[52] U.S. Cl. .................................................. 128/90
[58] Field of Search ............... 128/82–89 R, 128/90–91 R, 155, 156; 428/282; 66/195

[56] References Cited

U.S. PATENT DOCUMENTS

| | | | |
|---|---|---|---|
| 3,881,473 | 5/1975 | Corvi et al. | 128/90 |
| 3,908,644 | 9/1975 | Neinart | 128/90 |
| 4,143,655 | 3/1979 | Custer et al. | 128/90 |
| 4,427,002 | 1/1984 | Baron et al. | 128/83 |

*Primary Examiner*—John D. Yasko
*Attorney, Agent, or Firm*—Sprung, Horn, Kramer & Woods

[57] ABSTRACT

In a dressing material for the production of fixed dressings, comprising a raschel knit fabric carrier coated and/or impregnated with a resin which hardens in the presence of moisture and contains isocyanate groups, the improvement wherein the raschel fabric construction is such that the ratio of the mean distance between two warp threads to the mean distance between two weft threads is less than about 1.5.

10 Claims, 3 Drawing Figures

A     B     C

POLYURETHANE FIXED DRESSINGS WHICH HARDEN IN THE PRESENCE OF MOISTURE

The present invention relates to polyurethane fixed dressings which harden in the presence of moisture and are based on textile sheet-like structures, give a more comfortable fit and have improved strength.

Polyurethane fixed dressings which harden in the presence of moisture are described in, for example, German Auslegeschriften (German Published Specifications) Nos. 2,357,931 and 2,651,089. These dressings are flexible sheet-like structures, usually in tape form, as the carrier material, which are impregnated with an impregnating agent which contains isocyanate groups and hardens by reaction with water. These dressing materials can be applied in the same manner as conventional plaster bandages, that is to say the bandage is immersed in water and wound round and subsequently hardens to a rigid dressing.

Compared with plaster dressings, such polyurethane fixed dressings have, in particular, the following advantages: Low weight and volume, insensitivity to water, porosity and, in the case of a textile carrier material, outstanding transparency to X-rays.

A commercially available product of this type is the fixed dressing Baycast ® from Messrs. Bayer AG, in which a woven linen fabric of cotton is used as the flexible carrier material. This woven fabric has a weight per unit area of about 60 g/m$^2$, with a thread count of on average 11 threads/cm in the warp direction and 7 threads/cm in the weft direction. The ratio of the average distance between two warp threads to the average distance between two weft threads is thus about 0.6. Because they have a firm and relatively dense woven structure, bandages with a carrier material of woven linen fabric give fixed dressings of high strength and with a smooth surface. However, when woven linen fabric is used as the carrier material, the comfort is still not completely satisfactory as a result of a lack of extensibility of the woven fabric. Moreover, the dense and smooth surface of the hardened fixed dressing results in reduced porosity.

There have therefore been no lack of attempts to provide improved carrier materials for polyurethane fixed dressings. Such a dressing on a textile basis which fits more comfortably is, for example, CutterCast ® from Messrs. Cutter Laboratories, Inc., Berkeley, USA, in which a raschel fabric of cotton and polyester is used as the carrier material. This raschel fabric is built up such that, at a weight per unit area of about 80 g/m$^2$, the ratio of the average distance between two warp threads to the average distance between two partial weft threads is 2.7. The raschel fabric is rigid in the longitudinal direction, but has a crosswise extensibility of 40%. The bandages thus fit more comfortably than dressing materials based on a woven linen fabric which is rigid in the crosswise and longitudinal direction. However, the crosswise extensibility of 40% does not enable the dressing to be "drawn over", without creases, areas which are particularly difficult to be wrapped up, such as, for example, elbows or heels. Nevertheless, the crosswise extensibility of the raschel fabric, and the associated greater flexibility compared with the rigid woven linen fabric, means that the bandages give dressings which are less stiff, even in the hardened state. This means that, in order to achieve a fixed dressing of the same rigidity, more material is necessary if raschel fabric of the state of the art is used than if woven linen fabric is used.

A further possibility of making polyurethane fixed dressings fit more comfortably consists in using glass fiber carrier materials, such as have been disclosed, for example, in PCT Patent Application No. WO 81/00671. A commercial product which contains glass fiber bandages in the form of a similar raschel fabric with a crosswise extensibility of 30% is Scotchcast ® from Messrs. 3M, USA. The unsatisfactory crosswise extensibility of only 30% is indeed compensated by the good ability of the glass fibers to cling; and the material moreover hardens to give dressings having a high strength. However, the lack of transparency to X-rays, the sharp edges and the difficult removal of such glass fiber dressings are of great disadvantage.

There is thus the object of developing a carrier material for polyurethane fixed dressings which harden in the presence of moisture, which material combines a high transparency to X-rays with a high crosswise extensibility and high strength.

It has now been found that, surprisingly, all these properties can be combined in one material using a knitted fabric which is prepared from naturally occurring and/or synthetic fibers and is rigid in the longitudinal direction and highly extensible in the crosswise direction, and in which, at a weight per unit area of 40–150 g/m$^2$, preferably 50–100 g/m$^2$, the ratio of the average distance between two warp threads to the average distance between two weft threads is less than 1.5, and is preferably less than or equal to 1 and particularly preferably between 0.5 and 1.

The present invention thus relates to a dressing material for the production of fixed dressings, consisting of a raschel fabric of naturally occurring and/or synthetic fibers as the carrier material, which is coated and/or impregnated with a resin which hardens in the presence of moisture and contains isocyanate groups, characterized in that the ratio of the average distance between two warp threads to the average distance between two weft threads or partial weft threads in the raschel fabric is <1.5.

The dressing materials according to the invention have crosswise extensibilities of >100%. According to a particularly preferred embodiment, the weight per unit area of the raschel fabric is between 55 and 75 g/m$^2$, the distance ratio between the warp threads and weft threads is ≦1 and the crosswise extensibility is greater than 200%. The bandages according to the invention can therefore also be wound round critical areas rapidly and without creases. Surprisingly, the dressing materials according to the invention, in spite of their increased porosity, display a greatly increased strength compared with those of the state of the art, and in particular even though the weight per unit area of the knitted fabric in the bandages of the state of the art is up to 20% higher.

However, the fact that the strength of the knitted fabrics to be used according to the invention, even with a crosswise extensibility of >200% and with a high porosity, is superior to that of the rigid and relatively dense woven linen fabric is completely surprising. This was not to be expected inasmuch as the state of the art disclosed that, at approximately the same weights per unit area and degrees of impregnation, the rigidity of fixed dressings based on knitted fabrics is inferior to that of dressings based on woven fabrics, where the same textile base materials are used.

Both naturally occurring fibers, such as cotton or wool, and synthetic fibers, such as, for example, aliphatic or aromatic polyamides, polyesters, polyacrylonitrile, cellulose or carbon fibers, can be used for producing the knitted fabrics to be used according to the invention. Any desired mixtures of these materials can also be used.

Knitted fabrics of cotton fibers and/or polyester fibers are preferred according to the invention. The knitted fabrics can be produced by knitting techniques which are in themselves known, but the distance ratio of warp to weft (or partial weft) threads which is essential to the invention must be observed.

Examples of possible isocyanate resins which harden in the presence of moisture and with which the bandages of raschel fabrics are impregnated are products such as are described in the abovementioned German Auslegeschriften (German Published Specifications) Nos. 2,651,089 and 2,357,931. Any type of aliphatic, cycloaliphatic or, preferably, aromatic isocyanate containing at least two NCO groups can be used. The prepolymers having terminal NCO groups, which are known in themselves from polyurethane chemistry, that is to say reaction products of polyols (in particular polyester- or polyether-polyols) and excess polyisocyanate, are preferred. Products which are derived from phosgenated formaldehyde/aniline condensates and have optionally been modified by incorporation of urea, urethane or carbodiimide groups are preferred as the isocyanate components. The hardening reaction with water, which is effected by immersing the bandages in water or by exposing them to atmospheric humidity, is preferably accelerated by substances containing tertiary amine-nitrogen. Preferably, in this process the tertiary amine-nitrogen is incorporated into the prepolymer, such as is described in, for example, DAS (German Published Specification) No. 2,651,089. If appropriate, the isocyanate resins can also contain additives, for example fillers or light stabilizers (for example according to DE-OS (German Published Specification) No.2,921,163).

The degree of impregnation, which is defined as the ratio of resin weight to bandage weight, is preferably 50–200%, and particularly preferably 120–180%. In order to prevent premature hardening of the bandages by penetrating moisture, they are packed in containers which are impermeable to water vapor. Examples of such packaging materials are sealable plastic/aluminum laminates. Preferably, the bandages are also stored in these containers under exclusion of oxygen, that is to say, for example, in an atmosphere of nitrogen or another inert gas, as is described in DE-OS (German Published Specification) No. 3,033,659.

In the experimental section, the build-up of the knitted fabrics to be used according to the invention is compared, by way of example, with the build-up of the textile sheet-like structures of the state of the art. The moisture measurements of sample materials prepared and hardened under identical conditions are also compared.

The invention will be further described with reference to the drawing which is a schematic plan view of different textile carrier materials.

A is a woven linen fabric, B is a knitted fabric according to the state of the art and C is a raschel fabric to be used according to the invention. The materials are characterized by the parameters given in the following Table 1.

TABLE 1

| Woven fabric/knitted fabric | A | B | C |
|---|---|---|---|
| Weight per unit area (g/m$^2$) | 60 | 80 | 60 |
| Number of warp threads/cm | 12.1 | 2.5 | 5.8 |
| Number of weft threads/cm | 6.5 | 6.5 | 4 |
| wa (mm) | 0.84 | 4.0 | 1.8 |
| we (mm) | 1.5 | 1.5 | 2.4 |
| wa/we | 0.56 | 2.66 | 0.75 |
| Crosswise extensibility | 0 | 40 | 2.50 | wa = mean distance between two warp threads
we = mean distance between two weft threads The raschel fabric B consists of 60% of cotton fibers and 40% of polyester fibers; C consists of 100% cotton.

PREPARATION OF THE SAMPLE MATERIALS

The carrier materials A, B and C in the form of tapes 10 cm wide and 3 m long are impregnated with a resin which has been prepared from 100 parts by weight of a phosgenated aniline/formaldehyde condensation product having 30% by weight of NCO groups and a viscosity of 200 mPas at 25° C., and 32 parts by weight of a trihydroxypolyester (OH number 146, viscosity 1,200 mPas/25° C.) obtained by propoxylation of triethanolamine. The degree of impregnation, defined as the quotient of the resin weight and the bandage weight, is in each case 150%.

The tapes of woven fabric are immersed in water at 25° C. for 10 seconds, squeezed off and wound into a cylindrical sample material with an internal diameter of 4.6 cm. The bandages are then dried at room temperature for 24 hours.

MEASUREMENT OF THE MECHANICAL STRENGTH

The deflection of the sample material under a load of 50 kp is measured in a bending-measuring apparatus (manufacturer Messrs. Zwick, Federal Republic of Germany, model Z 423). For this, a wedge-shaped stamp is pressed onto the surface of the sample material parallel to the longitudinal axis of the cylindrical sample material and with a contact width of 31 mm.

The following deflections are obtained:

TABLE 2

| Sample material | A | B | C |
|---|---|---|---|
| Deflection (mm) | 4.8 | 9.6 | 3.8 |

Table 2 shows that the strength of the fixed dressing according to the invention exceeds that of the knitted fabric of the state of the art by 153% in spite of its lower weight per unit area, higher crosswise extensibility and porosity. The strength of the rigid and relatively dense woven linen fabric is also exceeded by 26%.

It will be appreciated that the instant specification and examples are set forth by way of illustration and not limitation, and that various modifications and changes may be made without departing from the spirit and scope of the present invention.

We claim:

1. In a dressing material for the production of fixed dressings, comprising a raschel knit fabric carrier coated and/or impregnated with a resin which hardens in the presence of moisture and contains isocyanate groups, the improvement wherein the raschel fabric has a weight per unit area of about 40 to 150 g/m$^2$ and its construction is such that the ratio of the mean distance between two warp threads to the mean distance between two weft threads is less than about 1.5.

2. A dressing material according to claim 1, wherein the raschel fabric comprises cotton.

3. A dressing material according to claim 1, wherein the raschel fabric comprises polyester fibers.

4. A dressing material according to claim 1, wherein the raschel fabric comprises a mixture of cotton and polyester fibers.

5. A dressing material according to claim 1, wherein the resin which hardens in the presence of moisture and is used for the impregnation is based on a polyisocyanate which has been obtained by phosgenation of an aniline/formaldehyde condensate.

6. A dressing material according to claim 1, wherein the resin is present in from about 120 to 180% by weight of the carrier.

7. A dressing material according to claim 1, wherein the ratio of the mean distance between two warp threads to the mean distance between two weft threads in the raschel fabric is $\leq 1$.

8. A dressing material according to claim 1, wherein the ratio of the mean distance between two warp threads to the mean distance between two weft threads in the raschel fabric is from about 0.5 to 1.

9. A dressing material according to claim 1, wherein the crosswise extensibility of the raschel fabric is greater than about 100%.

10. A dressing material according to claim 5, wherein the raschel fabric has a weight per unit area of about 50 to 100 $g/m^2$, and a crosswise extensibility greater than about 200%, comprises cotton and/or polyester fibers and the ratio of the mean distance between two warp threads to the mean distance between two weft threads in the raschel fabric is from about 0.5 to 1, the resin which hardens in the presence of moisture being based on a polyisocyanate which has been obtained by phosgenation of an aniline/formaldehyde condensate and being present in from about 120 to 180% by weight of the carrier.

* * * * *